(12) United States Patent
Miyamoto et al.

(10) Patent No.: US 6,227,145 B1
(45) Date of Patent: May 8, 2001

(54) HOUSEHOLD ANIMAL WASTE COLLECTION SHEET

(75) Inventors: Yuki Miyamoto; Kengo Ochi, both of Tokyo (JP)

(73) Assignee: Uni-Heartous Corporation, Tokyo (JP)

( * ) Notice: Subject to any disclaimer, the term of this patent is extended or adjusted under 35 U.S.C. 154(b) by 0 days.

(21) Appl. No.: 09/274,982

(22) Filed: Mar. 23, 1999

(30) Foreign Application Priority Data

Mar. 24, 1998 (JP) .................................................. 10-075843

(51) Int. Cl.[7] ............................. A01K 29/00; A61F 13/15
(52) U.S. Cl. ........................... 119/172; 119/163; 604/378
(58) Field of Search ................................... 119/169, 170, 119/850, 854, 172; 604/367, 378, 382

(56) References Cited

U.S. PATENT DOCUMENTS

| | | | |
|---|---|---|---|
| 4,800,841 | * | 1/1989 | Yananton et al. ..................... 119/169 |
| 4,852,518 | * | 8/1989 | Yananton ............................. 119/169 |
| 5,558,655 | * | 9/1996 | Jezzi et al. ........................... 604/378 |
| 5,669,894 | * | 9/1997 | Goldman et al. ..................... 604/378 |
| 5,681,300 | * | 10/1997 | Ahr et al. ............................. 604/367 |
| 5,715,772 | * | 2/1998 | Kamrath et al. ..................... 119/169 |

FOREIGN PATENT DOCUMENTS

| | | |
|---|---|---|
| 08-317740 | 3/1996 | (JP) . |
| 08-056518 | 5/1996 | (JP) . |
| WO94/06385 | 3/1994 | (WO) . |

* cited by examiner

*Primary Examiner*—Charles T. Jordan
*Assistant Examiner*—Elizabeth Shaw
(74) *Attorney, Agent, or Firm*—Darby & Darby

(57) ABSTRACT

A household animal waste collection sheet having a liquid permeable top sheet, a liquid impermeable backing sheet and an absorbent core interposed between the top sheet and the backing sheet, is disclosed. The absorbent core is formed of a pulp layer and particulate super-absorbent polymers disposed on both a top face and a bottom face of the pulp layer. This waste collection sheet has a high rate of liquid-absorption while preventing liquid from flowing backward to the top sheet. Further, the waste collection sheet has a high stiffness.

7 Claims, 3 Drawing Sheets

HOUSEHOLD ANIMAL WASTE COLLECTION SHEET

FIELD OF THE INVENTION

The present invention relates to a household animal waste collection sheet which is laid on a floor for collecting and disposing of a waste of a household animal. More specifically, it relates to a household animal waste collection sheet having excellent absorbing properties.

BACKGROUND OF THE INVENTION

In order to collect and dispose of wastes of household animals (pets to be kept indoors), a household animal waste collection sheet has been used. FIG. 3 shows a conventional household animal waste collection sheet 11. This household animal waste collection sheet 11 comprises a liquid permeable top sheet 12 such as a nonwoven fabric, a liquid impermeable backing sheet 13 such as a resin sheet, and an absorbent core 14 interposed between the top sheet 12 and the backing sheet 13. The absorbent core 14 is wrapped up in absorbent paper such as tissue paper. The absorbent core 14 is composed of a ground pulp layer 16 and particulate super-absorbent polymers 15 dispersed in the pulp layer 16. The pulp is excellent in a rate of liquid-absorption (swiftness) and the super-absorbent polymer is excellent in a liquid-absorption capacity. Accordingly, the absorbent core 14 can absorb a large amount of urine at a high rate of liquid-absorption.

However, a liquid-retentivity of the pulp is very low. Then, the urine once absorbed in the pulp tends to flow backward to the surface of the top sheet 12, and the top sheet 12 is disadvantageously wetted again.

SUMMARY OF THE INVENTION

The present invention is to solve the conventional problems. It is an object of the present invention to provide a household animal waste collection sheet which has excellent absorbing properties.

The object of the present invention is achieved by a household animal collection sheet comprising a liquid permeable top sheet, a liquid impermeable backing sheet, and an absorbent core interposed between the top sheet and the backing sheet, the absorbent core comprising a pulp layer and particulate super-absorbent polymers, the particulate super-absorbent polymers being disposed on both a top face and a bottom face of the pulp layer.

The household animal waste collection sheet of the present invention has a high rate of liquid-absorption due to the particulate super-absorbent polymers disposed on the bottom face of the pulp layer. Further, it can prevent the liquid once absorbed in the absorbent core from flowing backward to the surface of the top sheet, due to the particulate super-absorbent polymers disposed on the top face of the pulp layer. Still further, since both the top face and the bottom face of the pulp layer are covered with the super-absorbent polymers, the waste collection sheet has a high toughness. Accordingly, twisting or rolling of the sheet hardly occurs during use.

In the present invention, the rate of liquid-absorption of the super-absorbent polymers disposed on the bottom face is preferably higher than that of the super-absorbent polymers disposed on the top face. With such a structure, the rate of liquid-absorption of the waste collection sheet can be further increased. The rate of liquid-absorption of the super-absorbent polymers varies depending on whether or not they are crosslinked or on the particle size thereof. Therefore, it is preferable that the super-absorbent polymers disposed on the top face are crosslinked at surfaces thereof. Alternatively, it is preferable that the average particle size of the super-absorbent polymers disposed on the bottom face is smaller than that of the super-absorbent polymers disposed on the top face. In this case, for example, the average particle size of the super-absorbent polymers disposed on the bottom face is 80 meshes or more (0.175 mm or less), and the average particle size of the super-absorbent polymers disposed on the top face is 42 meshes or less (0.351 or more).

In the present invention, further, it is preferable that the super-absorbent polymers disposed on the top face are arranged in an intermittent or spotted pattern.

Still Further, it is preferable that the absorbent core is wrapped up in tissue paper.

DETAILED DESCRIPTION OF THE INVENTION

The present invention is now described with reference to the accompanying drawings.

Figure 1:
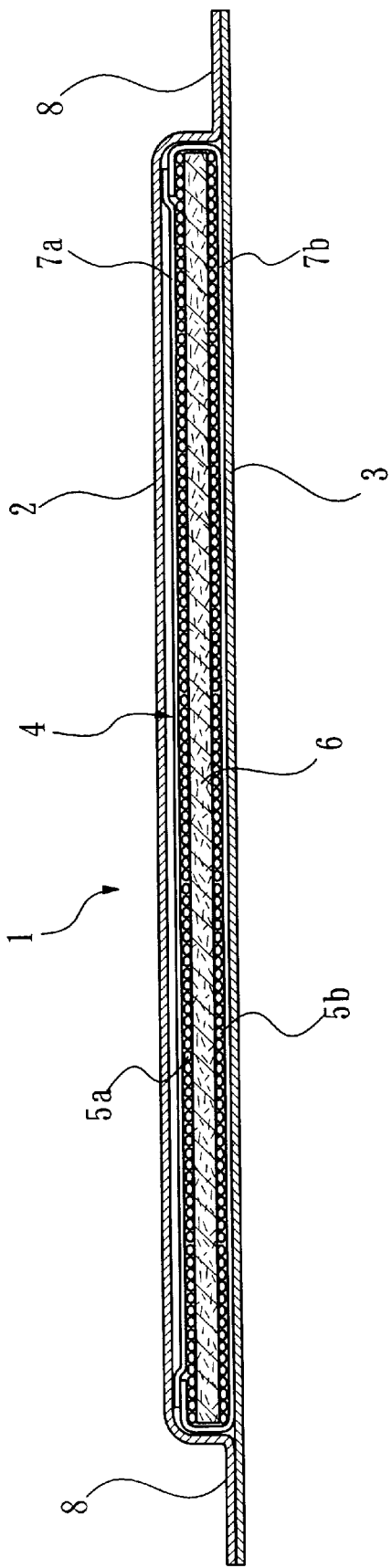
FIG. 1 is a sectional view of a household animal waste collection sheet of the present invention.

FIG. 1 is a sectional view of a household animal waste collection sheet 1 of the present invention. Although the household animal waste collection sheet 1 is drawn exaggeratedly in the thickness direction, it is actually a thin sheet having nearly a uniform thickness.

In the household animal waste collection sheet 1 of the present invention, as shown in FIG. 1, an absorbent core 4 is interposed between a liquid impermeable backing sheet 3 and a liquid permeable top sheet 2. The absorbent core 4 is composed of a pulp layer 6 and particulate super-absorbent polymers disposed on both the top face and the bottom face of the pulp layer 6. That is, particulate super-absorbent polymers 5a are disposed on the top face of the pulp layer 6, and particulate super-absorbent polymers 5b are disposed on the bottom face of the pulp layer 6. The top sheet 2 and the backing sheet 3 are bonded to each other, at edge portions 8 of the waste collection sheet 1. The waste collection sheet 1 can take a square, rectangular, oval or circular form in its plan view, and is made very thin, for example, less than 2 mm in the thickness direction thereof.

When a household animal excretes on this waste collection sheet 1, liquid such as unne permeates the top sheet 2 and reaches the absorbent core 4. In the absorbent core 4, the super-absorbent polymers 5a disposed on the top face of the pulp layer 6 can prevent liquid from flowing backward to the top sheet 2 more effectively as compared with conventional waste collection sheets. Further, the super-absorbent polymers 5b disposed on the bottom face of the pulp layer 6 can prevent the deterioration of the rate of liquid-absorption. Therefore, in the present invention, the liquid-retentivity can be enhanced while the rate of liquid-absorption is maintained.

The particulate super-absorbent polymers 5a, 5b can be made of polyacrylic acid, sodium polyacrylate, polyacrylamide, polyacrylonitrile, polyvinyl alcohol, an addition polymer of maleic anhydride, a polyether, a condensed polymer, a polysaccharide such as starch or cellulose, a protein such as collagen and the like. Examples of the particulate super-absorbent polymers include cross-linked compound of sodium polyacrylate, graft copolymers of starch having sodium polyacrylate and graft copolymers of cellulose having polyacrylonitrile chains. Among them, cross-linked compound of sodium polyacrylate or polyacrylic acid is preferable because it is less costly.

The pulp layer 6 can be made only of pulp such as ground pulp. The pulp may contain super-absorbent polymers.

The liquid permeable top sheet 2 is, for example, a point bond nonwoven fabric. The point bond nonwoven fabric is formed of synthetic fibers such as polyethylene fibers, polypropylene fibers or composite fibers of polyethylene and polypropylene. The point bond nonwoven fabric may further contain water-absorbent fibers such as rayon fibers.

Meanwhile, the liquid impermeable backing sheet 3 is a polyethylene (PE) film or a vinyl sheet.

The absorbent core 4 is preferably wrapped up in absorbent paper, for example, in two sheets of tissue paper 7a, 7b as shown in FIG. 1(A). The absorbent core 4 wrapped up in paper is easy to handle in the production stage. Further, the tissue paper 7b prevents the backing sheet 3 from being damaged by the particulate super-absorbent polymers 5b which are relatively hard. The tissue paper 7a beneath the top sheet 2 is preferably colored blue so as to give a clean feeling.

In a method of producing the household animal waste collection sheet 1, the absorbent core 4 is formed by sticking the particulate super-absorbent polymers 5a, 5b to the pulp layer 6 while containing a small amount of water, so as to prevent undesirable shift of the particulate super-absorbent polymers 5a, 5b in the waste collection sheet 1. The absorbent core 4 thus obtained can exhibit uniform absorbing properties at any parts thereof. Further, the absorbent core 4 thus obtained can be made sufficiently stiff. Consequently, even when a household animal walks on the waste collection sheet 1, it is possible to prevent the waste collection sheet 1 from being waved or wrinkled.

In the present invention, it is preferable that the rate of liquid-absorption of the super-absorbent polymers 5b disposed on the bottom face of the pulp layer 6 is higher than that of the super-absorbent resin 5a disposed on the top face of the pulp layer 6, or that the liquid-absorption capacity of the super-absorbent polymers 5b is higher than that of the super-absorbent polymers 5a. When the super-absorbent polymers 5b on the bottom face have the higher rate of liquid-absorption or the higher liquid-absorption capacity, the rate of liquid-absorption of the overall waste collection sheet 1 is further increased.

The rate of liquid-absorption of the super-absorbent polymers 5b can be made higher than that of the super-absorbent polymers 5a by varying the types of the super-absorbent polymers 5a, 5b.

For example, it is preferable that the individual particulate super-absorbent polymers 5a are crosslinked at the surfaces thereof while the super-absorbent polymers 5b are not crosslinked at all. The crosslinked super-absorbent polymers show a lower rate of liquid-absorption than the non-crosslinked super-absorbent polymers. Accordingly, the rate of liquid-absorption of the super-absorbent polymers 5b becomes higher than that of the super-absorbent polymers 5a. Further, the particulate super-absorbent polymers 5a crosslinked at the surfaces thereof hardly release the liquid once absorbed. Accordingly, the upper surface of the waste collection sheet 1 can be kept in a dry state even after it has absorbed liquid.

The rate of water-absorption may be adjusted by varying the extent of crosslinking of the super-absorbent polymers. For example, both the super-absorbent polymers 5a, 5b can be crosslinked at the surfaces thereof such that the degree of crosslinking of the super-absorbent polymers 5a is higher than that of the super-absorbent polymers 5b.

Incidentally, in general, when super-absorbent polymers are crosslinked, a gel strength of the super-absorbent polymers is increased. Accordingly, the super-absorbent polymers 5a, 5b can be selected depending on a gel strength, so as to adjust the rate of liquid-absorption.

In another way, the rate of liquid-absorption of the super-absorbent polymers 5b can be made higher than that of the super-absorbent polymers 5a by varying the particle sizes between the particulate super-absorbent polymers 5a, 5b. That is, the rate of water-absorption of the super-absorbent resin 5b can be made higher than that of the super-absorbent polymers 5a by making the average particle size of the super-absorbent polymers 5b smaller than that of the super-absorbent polymers 5a.

At this time, it is preferable that the average particle size of the super-absorbent polymers 5b is 80 meshes or more and the average particle size of the super-absorbent polymers 5a is 42 meshes or less. Since the super-absorbent polymers are hard in general, the backing sheet 3 is sometimes damaged or broken during production or during use when the particulate super-absorbent polymers having a large particle size are disposed in contact with the backing sheet 3. However, the super-absorbent polymers 5b having a particle size of 80 meshes or more effectively prevent the backing sheet 3 from being damaged or broken. On the other hand, the super-absorbent polymers 5a having a particle size of 42 meshes or less effectively prevent liquid once absorbed from flowing backward to the top sheet 2.

The particle size in terms of "meshes" herein used is determined according to the standard of Tyler, U.S.A. The particle size of 80 meshes or more is applied to particles which pass through a screen having an opening of 0.175 mm. That is, the particle size of 80 meshes or more means that the particle diameter is 0.175 mm or less. Further, the particle size of 42 meshes or less is applied to particles which are left on a screen having an opening of 0.351 mm. That is, the particle size of 42 meshes or less means that the particle diameter is 0.351 mm or more.

Figure 2A:
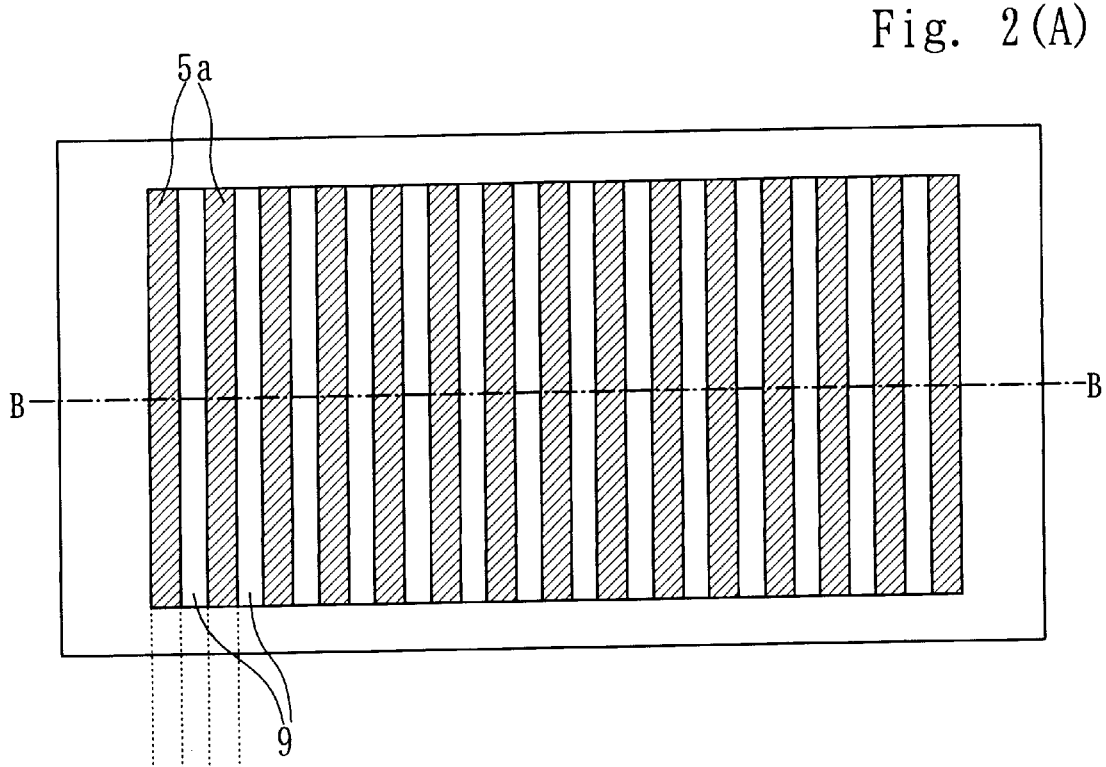
FIG. 2(A) is a plan view of another embodiment of the household animal waste collection sheet of the present invention.
Figure 2B:
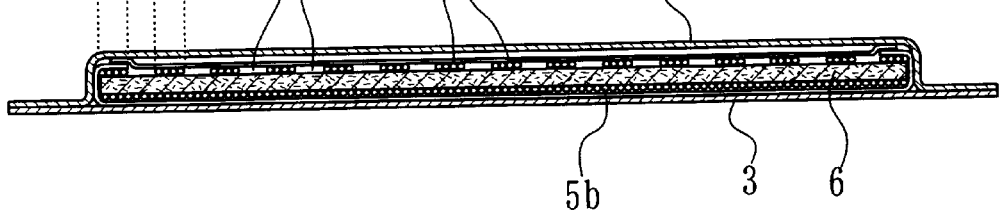
FIG. 2(B) is a sectional view taken along the line B—B of FIG. 2(A).
Figure 3:
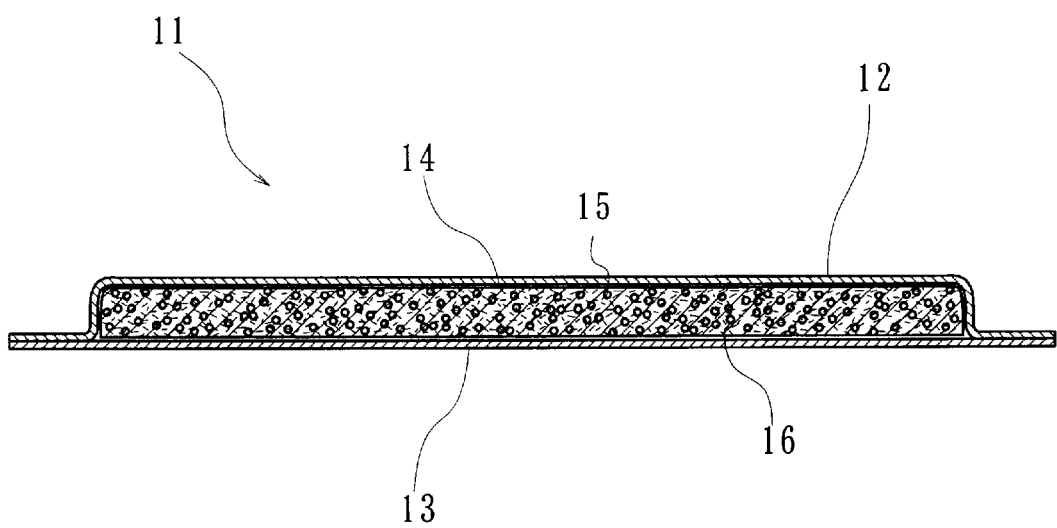
FIG. 3 is a sectional view of a conventional household animal waste collection sheet.

FIG. 2(A) is a plan view showing another embodiment of the household animal waste collection sheet of the present invention. FIG. 2(B) is a sectional view taken along the line B—B of FIG. 2(A). FIG. 2(B) is drawn exaggeratedly in the thickness direction.

As shown in FIGS. 2(A) and 2(B), the particulate super-absorbent polymers 5a may be arranged, not over the whole surface of the pulp layer 4 as in FIG. 1, but in a striped pattern. The super-absorbent polymers 5a are not provided in the areas indicated by 9 in FIG. 2(A). When a household animal excretes on this waste collection sheet, a part of liquid such as urine is directly absorbed into the pulp layer 6 through the areas 9, without being blocked by the super-absorbent polymers 5a (the rate of liquid-absorption of super-absorbent polymers is less than that of pulp). In this embodiment, further, the surface of the waste collection sheet can be dried faster than the embodiment shown in FIG. 1, because the total area where the super-absorbent polymers 5a are disposed is less than that in the embodiment shown in FIG. 1 (super-absorbent polymers are hard to dry). Accordingly, even when a household animal excretes repeatedly in the same position, liquid can be absorbed well.

It is advisable that the width of the area 9 is smaller than the average size of the sole of a household animal's foot so as to prevent the sole of the household animal's foot from being soiled with the liquid flowing backward onto the pulp layer 6 and floating in the areas 9.

The arrangement pattern of the particulate super-absorbent polymers 5a is not limited to the striped pattern shown in FIGS. 2(A) and 2(B). For example, they can be arranged in a dotted pattern or in a spiral pattern. In short, when the super-absorbent polymers 5a are arranged intermittently or spottedly, the same effect can be obtained.

EXAMPLE

The present invention will be illustrated more specifically with reference to the following Example and Comparative Examples.

The household animal waste collection sheet shown in FIG. 1 was prepared as Example. As the particulate super-absorbent polymers 5a, particles left on a screen of 40 meshes were used, and as the particulate super-absorbent polymers 5b, particles 4 passing through a screen of 80 meshes were used, each in amounts shown in Table 1. The amounts of the polymers were indicated in terms of g/m$^2$. At this time, the basis weight of the pulp layer 6 was 150 g/m$^2$. The waste collection sheet was pressed to have a thickness of 1.7 mm. A rate of liquid-absorption and a flow-back amount (the amount of liquid which turned back to the surface of the waste collection sheet) were measured with respect to this waste collection sheet.

(Measurement for Rate of Liquid-Absorption)

A cylinder having a diameter of 60 mm was mounted on the waste collection sheet. Artificial urine was charged into the cylinder at a dropping rate of 10 cc/sec using a burette. The lapsed time until the artificial urine was completely absorbed into the waste collection sheet was measured. The amount of the artificial urine charged was set at 80 cc. The artificial urine was a 0.9% by weight sodium chloride aqueous solution.

(Measurement for Flow-Back Amount)

After the artificial urine was charged, the sheet was left to stand for 3 minutes. 50 g of a stack of filter papers having a size of 10 cm×10 cm was prepared, and placed on the waste collection sheet, at a position where the artificial urine was charged. A load having a surface area of 10 cm×10 cm and a weight of 3.5 kg was placed on the filter paper, and it was allowed to stand for 3 minutes. Then, the amount of the artificial urine returned to the filter paper was measured.

As Comparative Examples 1 and 2, a waste collection sheet having super-absorbent polymers only on the top face of the pulp layer and a waste collection sheet having super-absorbent polymers only on the bottom face of the pulp layer were prepared in the same manner as in Example 1. The amounts of the super-absorbent polymers are shown in Table 1. The rate of liquid-absorption and the flow-back amount were measured in the same manner as in Example 1.

TABLE 1

| | Amount of Polymers (g/m$^2$) | | Rate of absorption (sec) | Flow-back amount (cc) |
| --- | --- | --- | --- | --- |
| | Top face 40 meshes | Bottom face 80 meshes | | |
| Example 1 | 32.0 | 14.0 | 22.0 | 0.2 |
| Com. Example 1 | 32.0 | — | 27.3 | 0.3 |
| Com. Example 2 | — | 32.0 | 21.8 | 17.0 |

While in the foregoing specification the present invention has been described in relation to preferred embodiments and many details have been set forth for purpose of illustration, it will be apparent to those skilled in the art that the present invention is susceptible to additional embodiments and that certain of the details described herein can be varied considerably without departing from the basic principles of the present invention.

As used herein, "comprises" and all its grammatical forms specifies the presence of stated features, integers, steps or components, but dose not preclude the presence or addition of one or more other features, integers, steps, components or groups thereof

What is claimed is:

1. A household animal waste collection sheet comprising:
   a liquid permeable top sheet,
   a liquid impermeable backing sheet, and
   an absorbent core interposed between the top sheet and the backing sheet, said absorbent core comprising a pulp layer and particulate super-absorbent polymers disposed on both a top face and a bottom face of the pulp layer, wherein:
   the rate of liquid-absorption of said super-absorbent polymers disposed on the bottom face is higher than that of said super-absorbent polymers disposed on the top face.

2. The household animal waste collection sheet as defined in claim 1, wherein:
   the absorbent core is formed by sticking said particulate super-absorbent polymers to the pulp layer when wet.

3. The household animal waste collection sheet as defined in claim 2, wherein:
   said super-absorbent polymers disposed on the top face are crosslinked at surfaces thereof.

4. The household animal waste collection sheet as defined in claim 2, wherein:
   the average particle size of said super-absorbent polymers disposed on the bottom face is smaller than that of said super-absorbent polymers disposed on the top face.

5. The household animal waste collection sheet as as defined in claim 4, wherein:
   the average particle size of said super-absorbent polymers disposed on the bottom face is 80 meshes or more, and the average particle size of said super-absorbent polymers disposed on the top face is 42 meshes or less.

6. The household animal waste collection sheet as defined in claim 2, wherein:
   said super-absorbent polymers disposed on the top face are arranged in one of an intermittent and spotted pattern.

7. The household animal waste collection sheet as defined in claim 2, wherein:
   the absorbent core is wrapped in tissue paper.

* * * * *